United States Patent
Sentmanat

(10) Patent No.: US 6,534,010 B2
(45) Date of Patent: Mar. 18, 2003

(54) APPARATUS FOR PROCESS LINE TESTING

(75) Inventor: Martin Lamar Sentmanat, Akron, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 216 days.

(21) Appl. No.: 09/732,055

(22) Filed: Dec. 7, 2000

(65) Prior Publication Data

US 2002/0072123 A1 Jun. 13, 2002

(51) Int. Cl.$^7$ ............................................... G01N 15/06
(52) U.S. Cl. ....................... 422/68.1; 422/129; 700/266; 73/54.22; 73/54.39
(58) Field of Search .......................... 422/55, 62, 68.1, 422/129; 73/54.27, 54.39, 54.28; 700/266

(56) References Cited

U.S. PATENT DOCUMENTS 4,584,882 A  *  4/1986  Tosaki ........................ 73/847
4,643,020 A  *  2/1987  Heinz ........................ 73/54.27

* cited by examiner

Primary Examiner—Jill Warden
Assistant Examiner—Sam P. Siefke
(74) Attorney, Agent, or Firm—David L. King; David E. Wheeler; Richard B. O'Planick

(57) ABSTRACT

An apparatus capable of characterizing the fluid content of chemicals in a reaction line comprises a rheometer. The apparatus can be connected to or included in a reaction flow stream, and has a retractable wall 26 that opens to provide an opening 28 that permits a portion of the reaction flow steam to enter into sampling chamber 12. The sample is isolated from the flow stream and rheometric data is obtained from the sample. In the method of the invention, data on the sample is collected and transferred to a computer. The computer is used to analyze the data, and optionally can be used to control reaction parameters in the reaction flow stream.

3 Claims, 6 Drawing Sheets

APPARATUS FOR PROCESS LINE TESTING

FIELD OF THE INVENTION

The invention relates to an inline testing device used for analyzing the state of a chemical reaction. In a specific embodiment, the testing device is a rheometer.

BACKGROUND OF THE INVENTION

Many chemical reactions are carried out in a continuous process, because of the efficiencies inherent in continuous processing related to yield and to eliminating the need to isolate intermediate products. In continuous chemical processing, it is sometimes important, in a multi-step chemical reaction, that the reaction reach a particular stage before parameters are changed, such as the addition of chemical compounds to the reaction, changes in temperature or atmospheric conditions, and the like. In the art, the status of the chemical reaction is often measured by removing a sample of material from the reaction process line, quenching the material, i.e. stopping the process of the chemical reaction, and analyzing the chemicals in the sample. The chemicals in the sample at that particular point define the status of the chemical reaction at that point, and tells the technician whether the reaction is proceeding as planned, and whether conditions are right for adding additional chemical reactants, or for changing the temperature, for example, in the processing line.

A common means for determining the state of reaction of a process is to measure certain physical properties of the compound which are a reflection of the nature of the material. Most chemicals, in a fluid state, exhibit rheological (flow) properties that are a function of the molecular size and structure of the material. For small chemical molecules with simple structure, the rheological properties of the material are fluid-like, independent of the rate and size of the applied deformation, and can be characterized in terms of a simple viscometric function such as a Newtonian viscosity. As molecular size and structure increases, a material's rheological properties become more complex and are dependent on the size and rate of the applied deformation. Polymeric materials are comprised of very long molecules and exhibit viscous (fluid-like) as well as elastic (solid-like) behavior, known to those skilled in the art as viscoelasticity. Although characterizing the viscosity of a polymer can be descriptive of its molecular size, a viscoelastic characterization which is more sensitive to molecular structure is required since a viscometric function is not descriptive of the elastic nature of the material. A more thorough treatment for describing the molecular mechanisms underlying the viscoelastic rheological behavior of polymeric fluids can be found in "Viscoelastic Properties of Polymers" by J. Ferry, Third Edition, John Wiley & Sons, N.Y. (1980).

In the chemical processing art, it is a continuing goal to completely automate the processing line. By that, it is meant that if analysis of the chemical reaction stream can be made at critical points, and the data from those critical points is fed into a computer, the computer can use the information to know when to adjust the reaction conditions as necessary, to assure that the chemical reaction goes as planned, which will improve the efficiency and yield of the chemical process. The nature of the analyzing equipment used at the critical points depends on the nature of the chemical reaction and the kind of data that will be most useful in analyzing the status of the chemical reaction. Since a chemical processing line is sometimes used for preparing more than one kind of chemical, and the materials used in the chemical processing line will change depending on the reaction, it is desirable that the analyzing equipment used be useful for a broad spectrum of chemical reactions.

It is an object of the present invention to provide a method and apparatus for analyzing the chemical or physical properties of a fluid in a reaction flow stream.

Other objects of the invention will be apparent from the following description and claims.

DESCRIPTION OF PRIOR ART

Various apparati have been developed for the use of on-line monitoring of a chemical process, most of which involve taking a side stream and pumping it through a capillary, slit, or rotating cylinder type of rheometer. These types of rheometers, however, typically provide only a viscometric and not a viscoelastic characterization of a fluid.

U.S. Pat. No. 4,468,953 (Garritano) describes an on-line concentric cylinder rotational rheometer for determining the vicoelastic properties of a fluid sampled from a process stream. The sampled fluid is introduced into the annular region of the concentric cylinders by means of a gear pump. The outer cylinder is made to oscillate about its axis of symmetry by means of a drive shaft and motor assembly, and the resultant torque on the inner cylinder is a measured by means of a torsion tube assembly that is hermetically sealed. Flow into the rheometer is distributed uniformly through the annulus so that the introduction of fresh sample flushes the previous fluid sample out of the annulus. However, in order to allow free oscillation of the outer cylinder,.the drive shaft requires the use of seals that are exposed to the thermal, chemical, and abrasive properties of the fluid. These seals require regular maintenance of the device and provide a possible source of failure during operation that could expose the surrounding environment to the hazards of the fluids being tested.

U.S. Pat. No. 4,643,020 (Heinz) describes a concentric cylinder process rheometer for characterizing the viscoelastic properties of a fluid that can be used either on-line or in the process stream. The sensing device consists of three concentric, thin-walled cylinders, the middle cylinder of which is made to oscillate about its axis of symmetry. The motion of the drive cylinder applies a shear to the fluid in the adjacent annular regions which causes a resultant torque on the drive cylinder that is measured on the drive shaft by means of a torsion tube and sensor assembly. Flexible bellows are used to seal the pivoting drive shaft from the fluid environment. Sample flushing out of the rheometer is uncontrolled, however, and the design does not allow for metered fluid flow into and out of the adjacent annuli to permit fresh sampling into the rheometer.

SUMMARY OF THE INVENTION

A method for analyzing the chemical or physical properties of a fluid in a reaction flow stream comprises the steps of (a) providing apparatus for analyzing fluid in a reaction flow stream, (b) isolating a sample of fluid in the apparatus for testing the physical and/or chemical properties of the fluid, (c) collecting data on the physical and/or chemical properties of a fluid from the apparatus, and storing the data in a computer, and (d) using the computer to control the parameters of the chemical reaction process in the reaction flow stream. In the method, the data from the apparatus for analyzing is used by the computer to determine current reaction conditions and to control the reaction parameters to maintain or achieve pre-selected reaction conditions.

The method may comprise the further step of selecting the apparatus for analyzing to be a rheometer, whereby the rheological viscoelastic properties of the reaction flow stream are analyzed.

The method may include the step of controlling parameters of the reaction selected from the group comprising temperature, flow rate, ratio of ingredients and mixtures thereof.

In the method, a sample of fluid is directed through the rheometer where the fluid is trapped between two opposed surfaces in the rheometer. One of the surfaces of the rheometer is connected to a transducer which measures the torque associated with the physical response of the sample to applied sample deformation.

The method may comprise the further steps of (a) closing the apparatus when a sample is within the analyzer and obtaining data on the sample while the sample is isolated from the reaction flow stream, (b) opening the apparatus to obtain a second sample and to return the first sample to the reaction flow stream, (c) closing the apparatus to obtain data on the second sample, and (d) continuing the process to substantially continuously monitor the properties of the reaction flow stream.

Also provided is an apparatus for inline testing of properties of a fluid in a reaction flow stream. The apparatus comprises a sampling chamber 12 adapted to traverse the flow stream. The sampling chamber comprises walls 26 containing a rotating platen 14 and an opposed torque measuring platen 16, the rotating platen 14 and the torque measuring platen 16 being separated by a gap 30. An actuator means 24 in association with sample platen 14 is adapted to widen and narrow gap 30. A motor 22 associated with the actuator is used for imparting motion to the sample platen 14. Torque measuring device 18 is associated with measuring platen 16.

The apparatus may further comprise a conduit module 20 for holding the sampling chamber 12, the conduit module 20 being adapted for installation into a conduit containing a reaction flow stream. In the illustrated embodiment, the apparatus has a wall 26 which is retractable such that wall 26 opens to provide an opening 28 to permit the reaction flow stream to pass through sampling chamber 12, whereby when wall 26 is re-deployed to cover opening 28, a sample contained within sampling chamber 12 is isolated from the flow stream, and when wall 26 is again retracted the sample is released to the flow stream.

In the illustrated embodiment, the apparatus has bellows 29 which expand and contract to accommodate different gap settings.

DETAILED DESCRIPTION OF THE INVENTION

Most chemicals, in a fluid state, exhibit viscous properties. Polymeric materials exhibit viscous (fluid-like) as well as elastic (solid-like) behavior, known to those skilled in the art as viscoelasticity. Elastomers exhibit greater elastic properties than other polymers. In the conception of the invention, the inventors proposed to use the known viscous nature of a fluid as an indicator of the contents of the fluid.

With reference now to FIGS. 1–6, the apparatus 10 of the invention is a rheometer which is adapted to be placed in line in a chemical processing reaction. In the illustrated embodiment, the apparatus includes a conduit module 20 which comprises a section of tubing which is adapted to be affixed in line to the tubing which is used for the chemical processing reaction, which encompasses a sampling chamber 12. From the description herein, it will be apparent to those skilled in the art that a sampling chamber 12 may be inserted into a chemical reaction line without the use of a conduit module 20.

Those skilled in the art will recognize that the reaction flow line can be a tap line off the main reaction stream.

Figure 4:
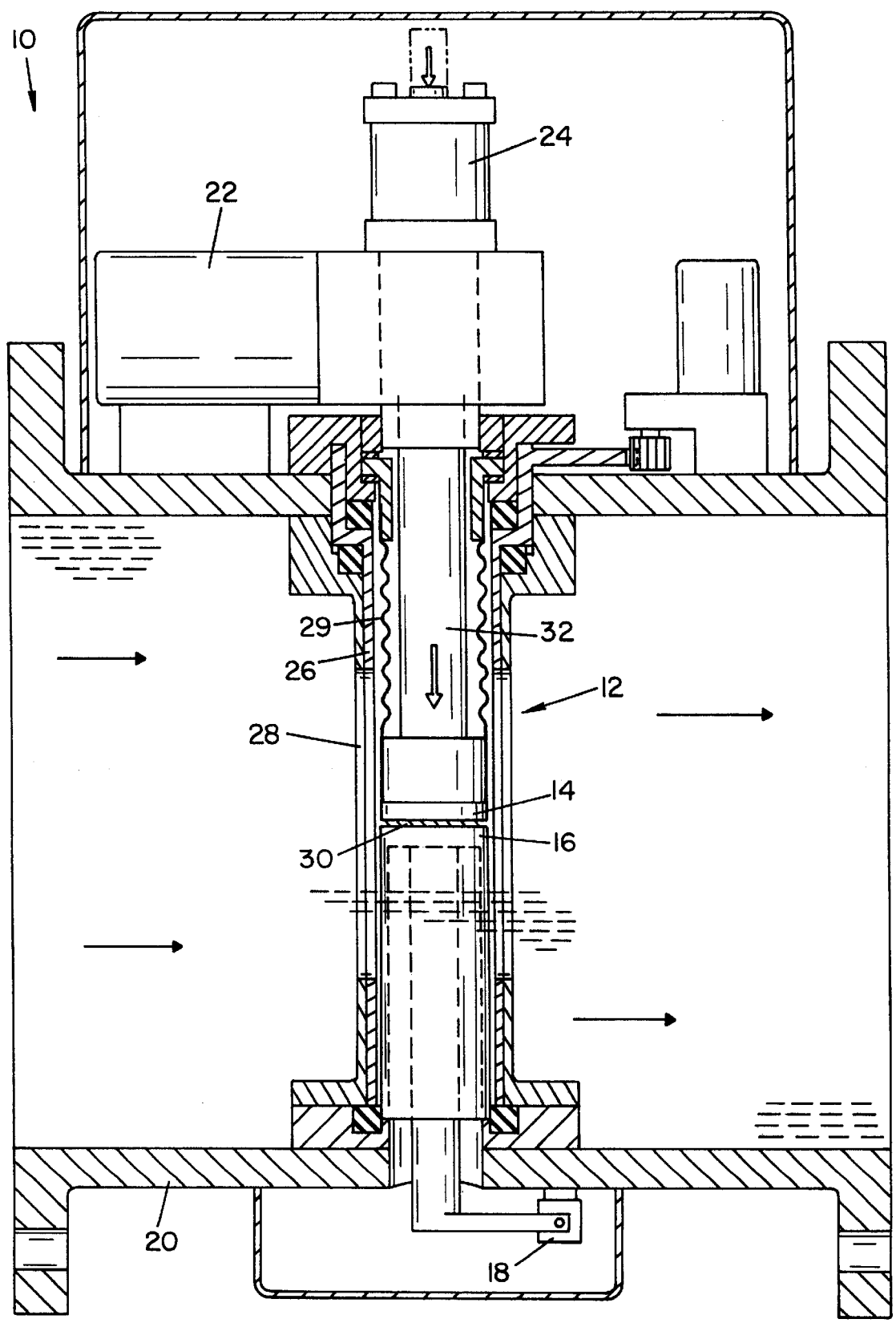
FIG. 4 illustrates the apparatus in a condition for testing a sample.

Sampling chamber 12 comprises walls 26, which in the illustrated embodiment are retractable, or rotatable to close opening 28 which enclose a flat rotating platen 14 and an opposed flat platen 16 for measuring torque. The rotating platen 14 is actuated by rotational motion stepper motor 22 through shaft 32, which connects rotational motion stepper motor 22 to rotating platen 14. Platen 16 is connected to a torque measuring device 18. Rotating platen 14 and opposed platen 16 are parallel and separated by a sample gap 30. When a sample is being measured, sample gap 30 is narrow as is illustrated in FIG. 4. When release of one sample, and the obtaining of a second sample is desired, rotating platen 14 is separated from opposed platen 16 by the action of extension/retraction actuator 24.

Figure 1:
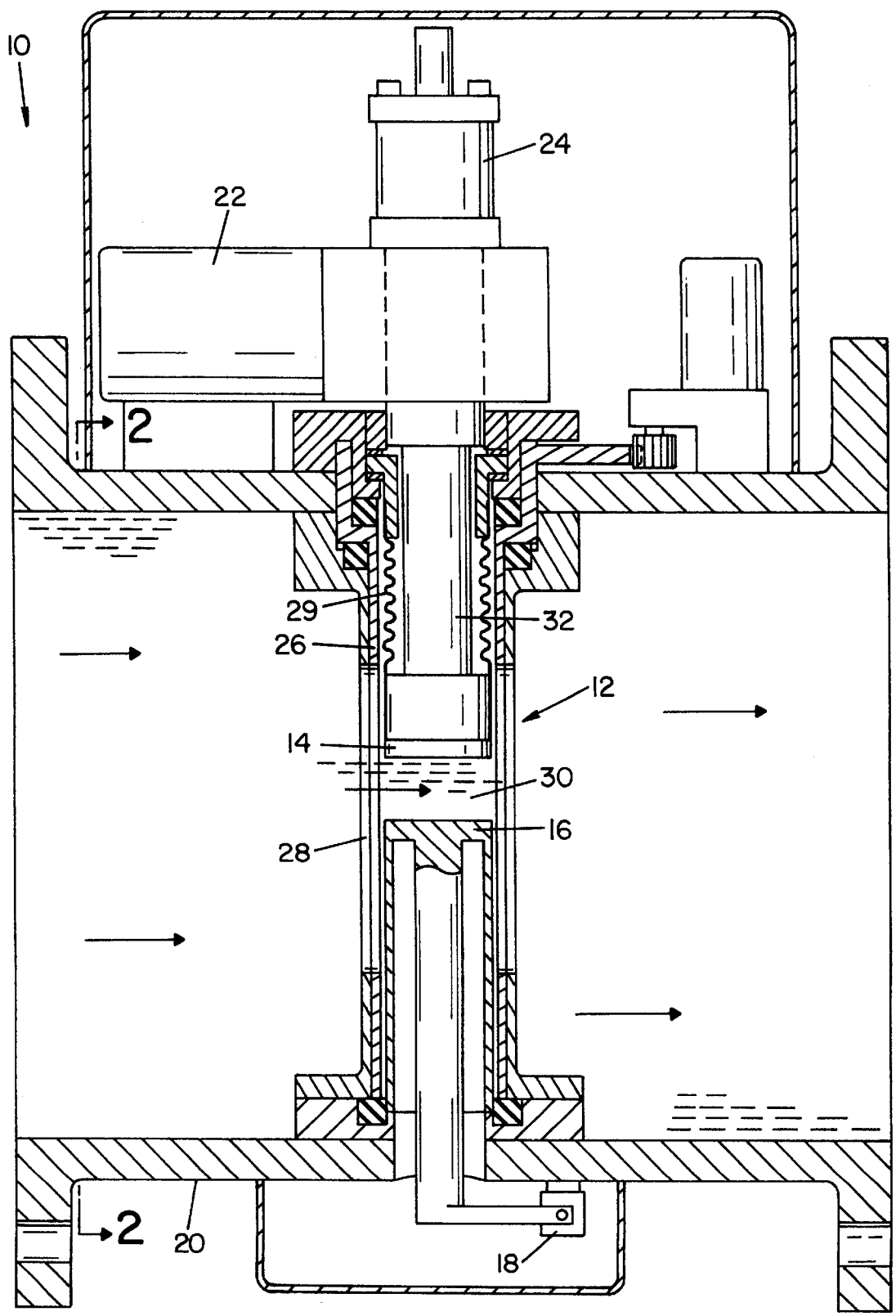
FIG. 1 illustrates a cross section of an apparatus of the invention (an inline rheometer) in an open condition for receiving a sample.
Figure 2:
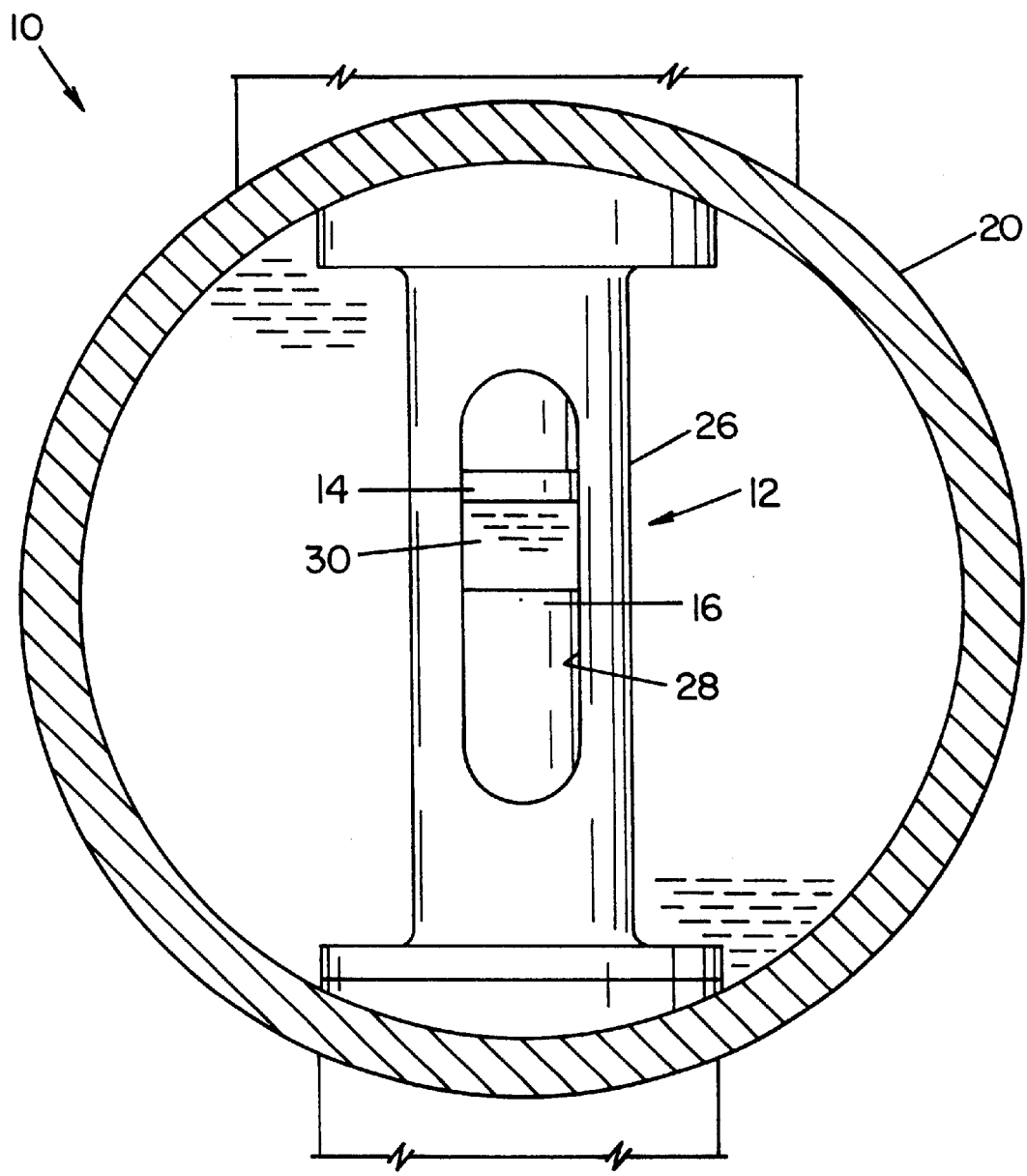
FIG. 2 illustrates the sample chamber of the apparatus of claim 1 with an open sample chamber, rotated at 90° along line 2—2.
Figure 3:
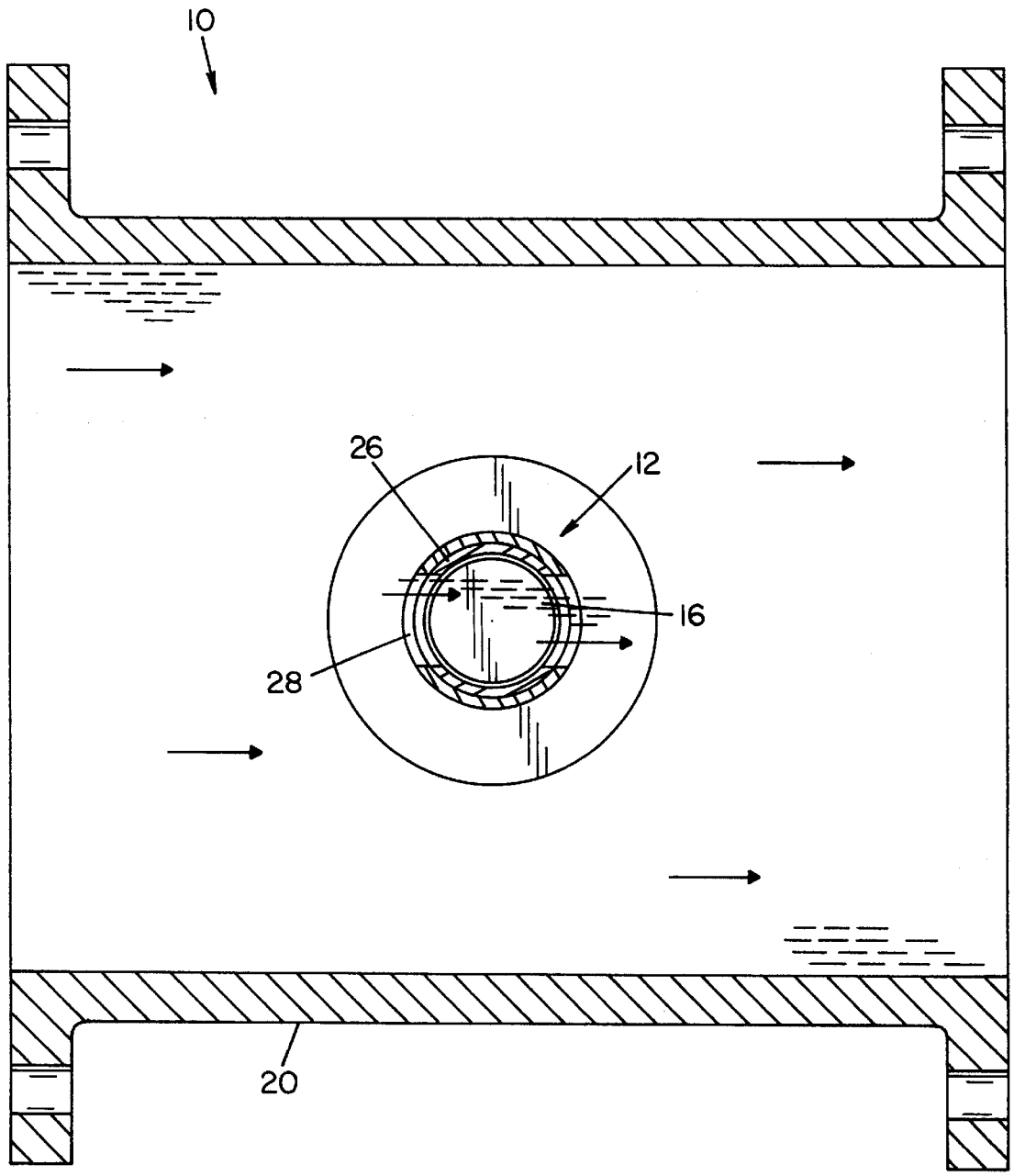
FIG. 3 illustrates a cross-section of a sample chamber and the actuator shaft.
Figure 5:
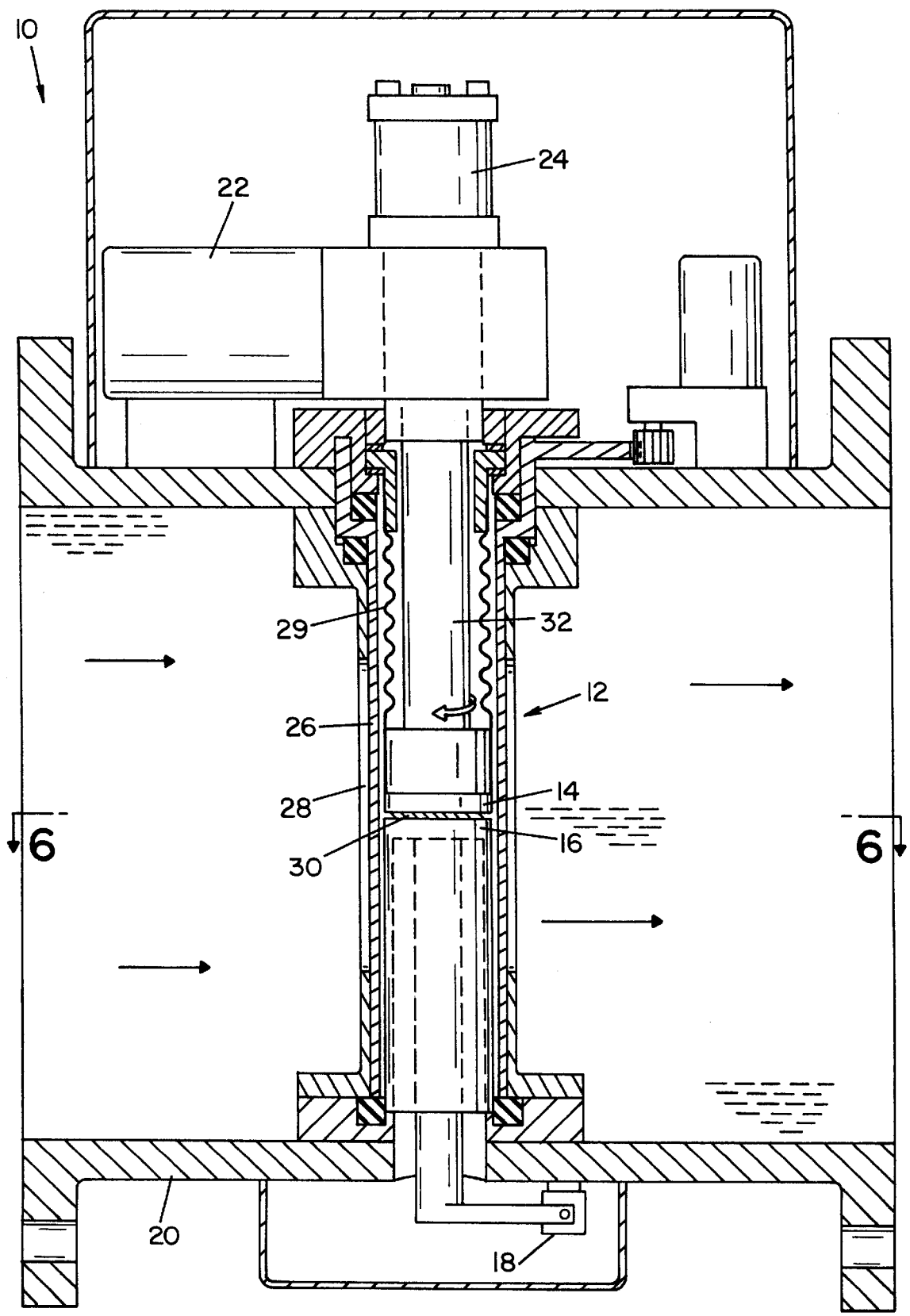
FIG. 5 illustrates the apparatus of the invention while obtaining data on a sample.
Figure 6:
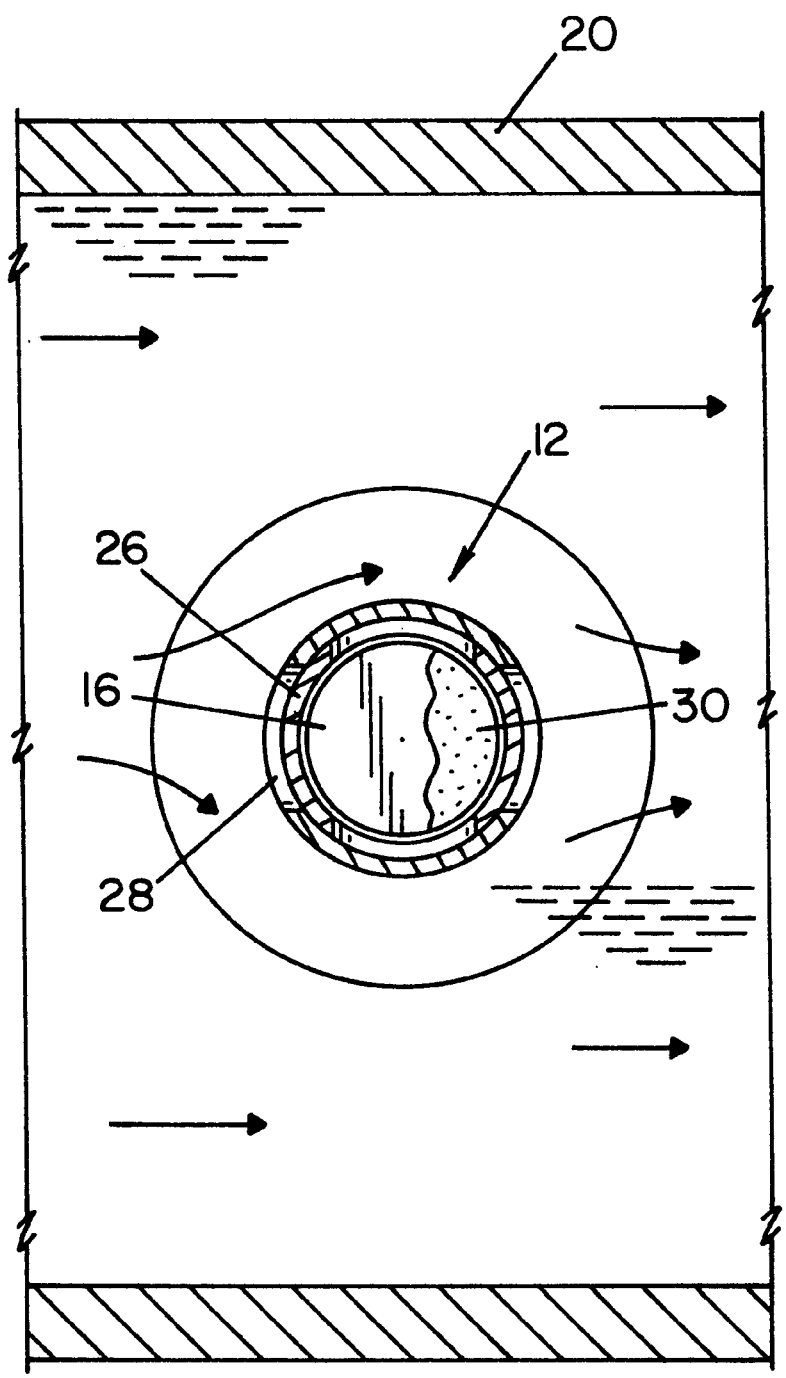
FIG. 6 illustrates the apparatus along the line 6—6 in FIG. 5.

In FIG. 5 the apparatus is illustrated having walls 26 enclosing the sample and the opposed platens 14,16. When it is desired to flush a sample on which data has been obtained from the apparatus, and to obtain a new sample, walls 26 are retracted as is illustrated in FIG. 4, to produce an opening 28 through which the chemical reactants in the reaction processing line may pass. With reference to FIG. 1, sample gap 30 is widened by actuation of extension/retraction actuator 24 to permit free flow of the chemical reactants through the sample chamber. Bellows 29 facilitates retraction of shaft 32 while maintaining a seal between the chemical reactants and the internal parts of the apparatus.

With reference now to FIGS. 1 to 6, in the method of the invention, the apparatus it is used by inserting sampling chamber 12 into a chemical reaction process line, optionally using a conduit module 20. When a sample for testing is obtained, the apparatus will be in the configuration described in FIG. 1, wherein sample gap 30 is wide, and opening 28 replaces walls 26 (FIG. 5). The wide sample gap 30 permits chemicals from the reaction process line to flow freely between rotating platen 14 and opposed (torque measuring) platen 16 through opening 28. When it is desirable to obtain a sample for obtaining data on the status of the chemical reaction, sample gap 30 is narrowed, as illustrated in FIG. 4, by extending actuator 24, as is illustrated in FIG. 4. Afterward, retracted walls 26 are closed, as illustrated in FIG. 5, to isolate the sample from the reaction flow line. Rheometric data is obtained by causing the rotational motion stepper motor 22 to cause platen 14 to rotate, and the torque transferred from rotating platen 14 to the sample trapped in sample gap 30, and from the sample to platen 16, is measured by the torque measuring device 18.

It is preferred that the sample be isolated from the reaction flow line so that stable data can be obtained. If the reaction chemical is permitted to continuously flow through sample gap 30, the motion of the sample will affect the torque measurements.

The width of sample gap 30 can be adjusted as desired for obtaining measurements on different chemicals having different viscous and/or different viscoelastic properties.

Once the data is obtained, walls 26 may be retracted, and actuator 24 retracted, to permit return of the sample to the reaction flow line, and the process may be repeated as often as necessary to obtain additional data.

Rheological data may be used to indicate whether or not specific desired compounds are being properly formed in the reaction process line at the proper point, and may be used as an indication of the completeness of the reaction. This information can also be used to indicate to the technician when the chemicals in the line have reached a stage where additional reactive chemicals may be added to the line.

When used in monitoring the status of polymeric reactions, the data can be used to indicate the state of polymerization. Such data may be particularly useful in the control of the development of elastomeric polymers.

When the data is obtained, the collected data can be transferred to a computer, and the information will indicate the status of the chemical reaction in the chemical processing line, i.e. the state of completion of the chemical reaction. This information can be used by the computer to change the flow rate of chemicals through the chemical processing line, change the temperature in the chemical processing line, or activate other parameters that will affect the rate of the reaction or to maintain the rate of the reaction.

While the invention has been specifically illustrated and described, those skilled in the art will recognize that the invention can be variously modified and practiced without departing from the spirit of the invention.

What is claimed is:

1. An apparatus for testing of properties of a fluid in a reaction flow stream comprising a sampling chamber adapted to traverse said flow stream, said sampling chamber comprising (a) walls containing a rotating flat platen and an opposed torque measuring flat platen, said rotating platen and said torque measuring platen being parallel and separated by a gap, (b) an actuator means in association with said sample platen adapted to widen and narrow said gap, (c) a motor associated with said actuator for imparting motion to said sample platen, and (d) a torque measuring device associated with said torque measuring platen; and wherein when taking a sample of the flow stream the wall is retractable such that wall opens to provide an opening to permit the reaction flow stream to pass through sampling chamber, whereby when wall is redeployed to cover opening, a sample contained within sampling chamber is isolated from the flow stream, and when wall is again retracted the sample is released to the flow stream.

2. The apparatus of claim 1 further comprising a conduit module for holding said sampling chamber, said conduit module being adapted for installation into a conduit containing a reaction flow stream.

3. The apparatus of claim 1 wherein bellows expands and contracts to accommodate different gap settings.

\* \* \* \* \*